(12) United States Patent
Yao et al.

(10) Patent No.: US 9,934,361 B2
(45) Date of Patent: Apr. 3, 2018

(54) METHOD FOR GENERATING HEALTHCARE-RELATED VALIDATED PREDICTION MODELS FROM MULTIPLE SOURCES

(71) Applicant: UNIVFY Inc., Los Altos, CA (US)

(72) Inventors: Mylene Yao, Los Altos, CA (US);
Wing H. Wong, Stanford, CA (US);
Bokyung Choi, San Francisco, CA (US)

(73) Assignee: UNIVFY Inc., Los Altos, CA (US)

( * ) Notice: Subject to any disclaimer, the term of this patent is extended or adjusted under 35 U.S.C. 154(b) by 221 days.

(21) Appl. No.: 13/631,988

(22) Filed: Sep. 29, 2012

(65) Prior Publication Data

US 2013/0085773 A1    Apr. 4, 2013

Related U.S. Application Data

(60) Provisional application No. 61/541,468, filed on Sep. 30, 2011.

(51) Int. Cl.
| | | |
|---|---|---|
| *G06Q 50/22* | (2012.01) | |
| *G06Q 50/24* | (2012.01) | |
| *G06F 19/00* | (2018.01) | |
| *G06Q 10/04* | (2012.01) | |

(52) U.S. Cl.
CPC ........ *G06F 19/3443* (2013.01); *G06F 19/345* (2013.01); *G06Q 10/04* (2013.01);
(Continued)

(58) Field of Classification Search
CPC ........ G06Q 50/22; G06Q 10/10; G06Q 10/06; G06Q 50/24; G06Q 10/063; G06Q 10/04;
(Continued)

(56) References Cited

U.S. PATENT DOCUMENTS

| | | |
|---|---|---|
| 4,816,257 A | 3/1989 | Buster et al. |
| 5,612,869 A | 3/1997 | Letz et al. |
| 5,619,991 A | 4/1997 | Sloane |
| 5,809,997 A | 9/1998 | Wolf |
| 5,812,984 A | 9/1998 | Goltra |
| 5,816,246 A | 10/1998 | Mirza |
| 5,832,450 A | 11/1998 | Myers et al. |

(Continued)

FOREIGN PATENT DOCUMENTS

WO    2010045463 A2    4/2010

OTHER PUBLICATIONS

Horvitz, From Data to Predictions and Decisions: Enabling Evidence-Based Healthcare, Computing Community Consortium, Version 6: Sep. 16, 2010.

(Continued)

*Primary Examiner* — Maroun Kanaan
(74) *Attorney, Agent, or Firm* — Karen Canaan; CanaanLaw, P.C.

(57) ABSTRACT

Provided is a method for generating prediction models from multiple healthcare centers. The method allows a third party to use data sets from multiple sources to build prediction models. By entering the data sets in a Model Deconstruction and Transfer (MDT) platform, a healthcare center may provide data to a third party without the need to de-identify data or to physically transfer any identifying or de-identified data from the healthcare center. The MDT platform includes a variable library, which allows the healthcare center to select variables that will be used to generate and validate the prediction model. Also provided is a method for compensating sources that contribute data sets based upon the percentage of clinical data that is used to generate a prediction model.

36 Claims, 2 Drawing Sheets

(52) U.S. Cl.
CPC ........ *F04C 2270/041* (2013.01); *G06Q 50/22* (2013.01); *G06Q 50/24* (2013.01)

(58) Field of Classification Search
CPC .... G06F 19/345; G06F 19/322; G06F 19/324; G06F 19/321
USPC ........................................................ 705/2, 3
See application file for complete search history.

(56) References Cited

U.S. PATENT DOCUMENTS

| | | | |
|---|---|---|---|
| 5,924,074 | A | 7/1999 | Evans |
| 6,347,329 | B1 | 2/2002 | Evans |
| 6,523,009 | B1 | 2/2003 | Wilkins |
| 6,529,876 | B1 | 3/2003 | Dart et al. |
| 6,597,946 | B2 | 7/2003 | Avrahami et al. |
| 6,600,696 | B1 | 7/2003 | Lynn |
| 7,076,437 | B1 | 7/2006 | Levy |
| 7,188,073 | B1 | 3/2007 | Tam et al. |
| 7,188,082 | B2 | 3/2007 | Keane et al. |
| 7,263,493 | B1 | 8/2007 | Provost |
| 7,275,220 | B2 | 9/2007 | Brummel et al. |
| 7,295,988 | B1 | 11/2007 | Reeves |
| 7,361,142 | B2 | 4/2008 | Suda |
| 7,392,199 | B2 | 6/2008 | Karlov et al. |
| 7,438,228 | B2 | 10/2008 | Robertson et al. |
| 7,461,079 | B2 | 12/2008 | Walker et al. |
| 7,643,969 | B2 | 1/2010 | Soto et al. |
| 7,685,000 | B1 | 3/2010 | Petit |
| 7,703,042 | B2 | 4/2010 | Brummel et al. |
| 7,730,024 | B2 | 6/2010 | Harinath |
| 7,853,456 | B2 | 12/2010 | Soto et al. |
| 8,160,977 | B2 | 4/2012 | Poulin |
| 2003/0017481 | A1 | 1/2003 | Golub et al. |
| 2005/0202426 | A1 | 9/2005 | Short et al. |
| 2006/0052945 | A1 | 3/2006 | Rabinowitz et al. |
| 2006/0173663 | A1 | 8/2006 | Lagheier et al. |
| 2007/0027636 | A1 | 2/2007 | Rabinowitz et al. |
| 2007/0053563 | A1 | 3/2007 | Tu et al. |
| 2007/0055552 | A1 | 3/2007 | St. Clair et al. |
| 2007/0082328 | A1 | 4/2007 | Williams et al. |
| 2007/0130206 | A1 | 6/2007 | Zhou et al. |
| 2007/0162992 | A1 | 7/2007 | Burns |
| 2007/0178501 | A1 | 8/2007 | Rabinowitz et al. |
| 2007/0192134 | A1 | 8/2007 | Littenberg et al. |
| 2007/0238111 | A1 | 10/2007 | Cibelli et al. |
| 2008/0040151 | A1* | 2/2008 | Moore ............................. 705/2 |
| 2008/0133275 | A1 | 6/2008 | Haug et al. |
| 2008/0162992 | A1 | 7/2008 | Moser et al. |
| 2008/0163824 | A1 | 7/2008 | Moser et al. |
| 2009/0029375 | A1 | 1/2009 | Jupe et al. |
| 2009/0259491 | A1 | 10/2009 | Busch |
| 2010/0036192 | A1 | 2/2010 | Yao et al. |
| 2010/0049689 | A1 | 2/2010 | Jorg et al. |
| 2010/0112605 | A1 | 5/2010 | Paul et al. |
| 2010/0138199 | A1 | 6/2010 | Soto et al. |
| 2011/0119212 | A1* | 5/2011 | De Bruin et al. ............. 706/12 |
| 2011/0173018 | A1 | 7/2011 | Hoffner et al. |
| 2011/0288789 | A1 | 11/2011 | Rabinowitz et al. |
| 2011/0313790 | A1 | 12/2011 | Yao |
| 2012/0016184 | A1 | 1/2012 | Yao |
| 2013/0246097 | A1* | 9/2013 | Kenney et al. .................. 705/3 |

OTHER PUBLICATIONS

American Society for Reproductive Medicine (ASRM), Guidelines on Number of Embryos Transferred, Fertility and Sterility 90:S163-S164 (2008).

Banerjee et al., Deep Phenotyping to Predict Live Birth Outcomes in In Vitro Fertilization, PNAS 107 (31):13570-13575 (2010).

Bonduelle et al., A Multi-Centre Cohort Study of the Physical Health of 5-Year-Old Children Conceived After Intracytoplasmic Sperm Injection, In Vitro Fertilization and Natural Conception, Human Reproduction 20(2):413-419 (2005).

Friedman, Greedy Function Approximation: A Gradient Boosting Machine, IMS 1999 Reitz Lecture, Feb. 24, 1999 (modified Mar. 15, 2000 and Apr. 15, 2001).

Friedman, Stochastic Gradient Boosting, Stanford University Technical Paper, Mar. 26, 1999.

Friedman, Tutorial: Getting Started in MART with R, Stanford University Technical Paper, May 13, 2002.

Friedman et al., Multiple Additive Regression Trees with Application in Epidemiology, Statistics in Medicine 22:1365-1381 (2003).

Hseih et al., Decreased Expression of Mitochondrial Genes in Human Unfertilized Oocytes and Arrested Embryos, Fertility and Sterility 81 Supp. 1, pp. 912-918, Mar. 2004.

Jun et al., Defining Human Embryo Phenotypes by Cohort-Specific Prognostic Factors, PLoS ONE 3(7):e2562, pp. 1-7 (2008).

Kalu et al., Reducing Multiple Pregnancy in Assisted Reproduction Technology: Towards a Policy of Single Blastocyst Transfer in Younger Women, British Journal of Obstetrics and Gynecology (BJOG) 115:1143-1150 (2008).

Khalaf et al., Selective Single Blastocyst Transfer Reduces the Multiple Pregnancy Rate and Increases Pregnancy Rates: a Pre- and Postintervention Study, British Journal of Obstetrics and Gynecology (BJOG) 115:385-390 (2008).

Li et al., Analysis of Gene Expression in Single Human Oocytes and Preimplantation Embryos, Biochem. and Biophys. Res. Comm. 340(1):48-53 (2006).

Martin et al., Births: Final Data for 2006, National Vital Statistics Reports (NVSR) 57(7):1-102 (2009).

Osterman et al., Expanded Health Data From the New Birth Certificate, 2006, National Vital Statistics Reports (NVSR) 58(5):1-24 (2009).

Passmore et al., Assessing Decision Tree Models for Clinical In-Vitro Fertilization Data, Technical Report TR03-296, Department of Computer Science and Statistics, University of Rhode Island, Mar. 2004.

Pinborg et al., Neonatal Outcome in a Danish National Cohort of 8602 Children Born After In Vitro Fertilization or Intracytoplasmic Sperm Injection: The Role of Twin Pregnancy, Acta Obstet Gynecol Scand 83: 1071--1078 (2004).

Styer et al., Single-Blastocyst Transfer Decreases Twin Gestation Without Affecting Pregnancy Outcome, Fertility and Sterility 89(6):1702-1708 (2008).

Sunderam et al., Assisted Reproductive Technology Surveillance—United States, 2006, Morbidity and Mortality Weekly Report (MMWR) 58(SS05):1-25 (2009).

Sutcliffe et al., Outcome of Assisted Reproduction (Review), Lancet 370:351-59 (2007).

Van Voorhis, In Vitro Fertilization, The New England Journal of Medicine 356:379-86 (2007).

International Search Report and Written Opinion for counterpart PCT/US2012/058189, mailed from WIPO on Feb. 11, 2013.

EP Supplementary Search Report for counterpart application EP 12835860 dated Aug. 18, 2015.

Park and Kargupta, Distributed Data Mining: Algorithms, Systems, and Applications, Department of Computer Science and Electrical Engineering, University of Baltimore, MD, pp. 1-22 (2002).

Luo et al., A Distributed Approach to Enabling Privacy-Preserving Model-Based Classifier Training, Knowl Inf Syst 20:157-185 (2009).

Khatri et al., Architecture for Preserving Privacy During Data Mining by Hybridization of Partitioning on Medical Data, 2010 Fourth Asia International Conference on Mathematical/Analytical Modelling and Computer Simulation, pp. 93-97, IEEE Computer Society (2010).

* cited by examiner

METHOD FOR GENERATING HEALTHCARE-RELATED VALIDATED PREDICTION MODELS FROM MULTIPLE SOURCES

CROSS-REFERENCE TO RELATED APPLICATIONS

This application claims priority to U.S. Provisional Application No. 61/541,468, filed on Sep. 30, 2011, which is incorporated herein in its entirety.

TECHNICAL FIELD

The present invention relates generally to healthcare prediction models. More specifically, the present invention relates to healthcare-related prediction models generated from multiple sources.

BACKGROUND OF THE INVENTION

In recent years, there has been significant effort by the healthcare industry to improve clinical outcomes to patients by providing evidence-based personalized decision support systems and establishing clinical protocols that address the characteristics of both individual patients and patient populations. The healthcare industry has also aimed to provide greater value to patients and their payers (i.e., their insurance carriers and employers) by using evidence-based personalized decision support systems to consider health benefits and cost-effectiveness when recommending treatment regimens.

The above-mentioned efforts by the healthcare industry have been facilitated through the implementation and adoption of health related information technologies (IT), which have led to patient and physician access to electronic medical records and the exchange of electronic data among healthcare providers, laboratories, pharmacies, healthcare managers, and healthcare administrators. Healthcare-related IT platforms have also been instrumental in carrying out biodiscovery, the translation of genetic and molecular data to clinical applications, and the development of prediction models for identifying healthcare-related issues and/or disease outcomes.

In theory, the implementation of healthcare-related prediction models should have a significant impact on healthcare quality and delivery; however, in practice, the types of EMR-generated prediction models and their utility have remained limited to date. Large data sets amassed from multiple data sources, such as healthcare facilities, are often required to build meaningful prediction models with clinical utility. Because the collection, processing, and analysis of such large data sets requires the expenditure of significant human and monetary resources, the benefits of such prediction models remain outside the reach of entities of modest size and/or resources.

In addition to the challenges inherent in physically amassing large quantities of data, the implementation of prediction models also faces challenges related to the protection of personal identifiers that are present in the data sets. Currently, the processing of healthcare information from multiple healthcare facilities to build prediction models requires the transfer of the health data beyond the physical and network boundaries of each healthcare facility. The presence of personal identifiers in the data poses great administrative, logistical, and contractual hurdles to healthcare facilities and any third party entity that is involved in the data processing or analysis. The presence of personal identifiers also raises liability issues and increase the facilities costs to protect against liability. Although personal identifiers may be removed, there are also significant logistical, technical, and financial costs incurred by producing de-identified data sets while preserving the integrity of the data. Because such processes are time-consuming and costly, they inhibit the development of healthcare prediction models.

SUMMARY OF THE INVENTION

The present invention improves upon what is known in the art by providing methods to generate and validate healthcare prediction models based upon healthcare data obtained from multiple sources, without the need to de-identify or transfer clinical data beyond the physical and network boundaries of healthcare facilities. The validated prediction models of the present invention are based upon multiple variables that are capable of being applied to diverse patient populations.

In one embodiment of the invention, there is provided a method of generating a prediction model for a health outcome of interest comprising the steps of: (a) providing more than one healthcare centers with a Model Deconstruction Transfer (MDT) platform comprised of a variable library (VL), wherein each healthcare center enters at least one data set relevant to the health outcome of interest into the MDT platform and selects variables from the VL that are relevant to the health outcome of interest; and (b) generating at least one prediction model ($PM_0$) for each healthcare center from the MDT platform, wherein each $PM_0$ is based upon the selected variables.

In another embodiment, the method further comprises the steps of: (c) generating a Model Component Library (MCL) from each $PM_0$, wherein the MCL comprises components that result from deconstruction of each $PM_0$, and (d) generating at least one second prediction model ($PM_1$) from the MCL, wherein the at least one $PM_1$ is designed to predict the probability of the health outcome of interest in a population of patients collectively representative of each healthcare center. The at least one $PM_1$ may be generated from the MCL by using individual MCL components as variables in the at least one $PM_1$ with differential weighting. A single MCL component may be used more than once in a single $PM_1$. Further, each use of a single MCL component may be subject to a different statistical function.

In another embodiment of the invention, there is provided a method of generating a prediction model for a health outcome of interest comprising the steps of: (a) obtaining at least one data set relevant to the health outcome of interest from more than one healthcare centers; (b) selecting variables from each data set that are relevant to the health outcome of interest; (c) generating at least one first prediction model ($PM_0$) for each healthcare center based upon differential weighting of the at least one data set variables, wherein the at least one $PM_0$ is generated using a computing device; (d) generating a Model Component Library (MCL) from each $PM_0$, wherein the MCL comprises components that result from deconstruction of each $PM_0$; and (e) generating at least one second prediction model ($PM_1$) from the MCL based upon differential weighting of the MCL components relevant to the health outcome of interest. In one embodiment, the more than one healthcare centers may enter the at least one data set into a Model Deconstruction Transfer (MDT) platform comprising a variable library (VL).

In a further embodiment, the foregoing methods further comprise the step of: obtaining at least one second data set from at least one of the more than one healthcare centers, wherein the at least one second data set comprises healthcare data that pertains to a group of patients from a healthcare center that is not represented in the MCL and is non-redundant and unrelated to data used to generate the MCL.

In another embodiment, the foregoing methods further comprise the step of: obtaining at least one second data set from at least one of the more than one healthcare centers, wherein the at least one second data set comprises healthcare data pertaining to a group of patients from a healthcare center that is represented in the MCL, wherein the at least one second data set is non-redundant to the at least one data set of step (a) and the healthcare data that comprises the at least one second data set is unrelated to the healthcare data used to generate the MCL.

In further embodiments, the at least one second data set comprises a training set, a test set, or a combination of a test set and a training set. In one embodiment, the at least one second data set may be divided into training and test sets chronologically according to the year of origin of the healthcare data.

In another embodiment, the at least one $PM_1$ comprises MCL components that are selected based upon the performance of the at least one $PM_1$ to predict probabilities of the healthcare outcome in the training set or the test set.

In further embodiments, the at least one $PM_1$ is generated from the MCL by using individual MCL components as variables in the at least one $PM_1$ with differential weighting. A single MCL component may be used more than once in a single $PM_1$. Further, each use of a single MCL component may be subject to a different statistical function.

In another embodiment, the VL comprises variables selected from the group consisting of patient demographics, patient insurance policy status, patient billing data, patient family history, patient laboratory results, patient imaging results, patient pathology results (tissue biopsies), patient immunopathology results, patient cytology results, patient cytogenetic results, patient gene expression, patient metabolic panels, patient metabolic profiles, patient genomic data, patient response to procedures, patient medications, patient therapeutic regimens, patient acute care parameters, patient ambulatory monitoring; frequency of outpatient visits, frequency of emergency visits, frequency of hospital admissions, frequency of hospital re-admissions; quality of life assessments; clinical characteristics (clinical signs and symptoms), clinical diagnoses, clinic inpatient procedures, clinic outpatient procedures; monitoring for cancer recurrence, psychiatric assessments; and CPT (current procedural technology) diagnostic codes.

In a further embodiment, the MCL components are selected from the group consisting of patient demographics, patient insurance policy status, patient billing data, patient family history, patient laboratory results, patient imaging results, patient pathology results (tissue biopsies), patient immunopathology results, patient cytology results, patient cytogenetic results, patient gene expression, patient metabolic panels, patient metabolic profiles, patient genomic data, patient response to procedures, patient medications, patient therapeutic regimens, patient acute care parameters, patient ambulatory monitoring; frequency of outpatient visits, frequency of emergency visits, frequency of hospital admissions, frequency of hospital re-admissions; quality of life assessments; clinical characteristics (clinical signs and symptoms), clinical diagnoses, clinic inpatient procedures, clinic outpatient procedures; monitoring for cancer recurrence, psychiatric assessments; and CPT (current procedural technology) diagnostic codes.

In another embodiment, the health outcome is selected from the group consisting of poor treatment response, worsening of a condition, rate of disease progression, probability of success following an interventional procedure, probability of failure following an interventional procedure, probability of complications following an interventional procedure, readmission to emergency services for a specific condition, readmission to a hospital for a specific condition, development of co-morbidities, and combinations of any of the foregoing.

In a further embodiment, the MDT platform is provided in an electronic storage medium, which may be selected from the group consisting of an external hard drive, a CD ROM, a USB memory device, an electronic mobile device, desktop computer, a server, a VPN, a secure internet website, and a software product that is downloadable from the internet with security features. The server may be selected from an on-site local server at the healthcare center and an off-site collocation or cloud server controlled by the healthcare center.

In another embodiment, the computing device may be programmed to run statistical techniques selected from the group consisting of machine learning, logistic regression, linear regression, non-linear regression, and combinations of any of the foregoing.

In a further embodiment, the at least one $PM_0$ is generated using statistical techniques selected from the group consisting of machine learning, logistic regression, linear regression, non-linear regression, and combinations of any of the foregoing. The machine learning technique may be selected from the group consisting of classification tree methods, LASSO (least absolute shrinkage and selection operator), Bayesian network modeling, and combinations of any of the foregoing. An example of a classification tree method is a boosted tree method.

In another embodiment, at least two $PM_1$ are generated, ranked, and selected according to model performance parameters selected from the group consisting of posterior log likelihoods, predictive power based upon posterior probability of an event, predictive power based upon estimated errors of prediction, dynamic range of predicted probabilities, reclassification, frequency of predicted probabilities, cross-validation error, number of model components required, and discrimination.

In a further embodiment, the at least one $PM_0$ and/or the at least one $PM_1$ may be validated by a validation test originating from at least one of the more than one healthcare centers. In one embodiment, the at least one $PM_0$ and/or the at least one $PM_1$ may be validated by a test data set originating from one or more of the healthcare centers. In another embodiment, the at least one $PM_1$ may be validated against a test data set originating from a healthcare center to which the at least one $PM_1$ will be applied.

In a further embodiment, performance of the validated at least one $PM_0$ and/or validated at least one $PM_1$ may be measured by comparison against performance of a control model. In one embodiment, the comparison of the validated at least one $PM_0$ and/or validated at least one $PM_1$ may be carried out by applying statistical criteria selected from the group consisting of predictive power based on posterior log likelihoods, predictive power based upon posterior probability of an event, predictive power based upon estimated errors of prediction, dynamic range of predicted probabilities, reclassification, frequency of predicted probabilities, cross-validation error, number of model components required, and discrimination. The machine learning techniques may be selected from the group consisting of classification tree methods, LASSO (least absolute shrinkage and selection operator), Bayesian network modeling, and combinations of any of the foregoing. The classification tree method may be a boosted tree method.

In another embodiment, there is provided a method of compensating a healthcare center based upon data provided by the healthcare center for use in the generation of a prediction model for a health outcome comprising the steps of: (a) providing the healthcare center with at least one data set comprising a variable library (VL), wherein the healthcare center selects variables from the VL that are relevant to a health outcome of interest; (b) generating a first prediction model ($PM_0$) for the healthcare center based upon the VL variables; (c) generating a Model Component Library (MCL) from the at least one $PM_0$, wherein the MCL comprises components that result from deconstruction of the at least one $PM_0$; (d) generating at least one second prediction model ($PM_1$) for the health outcome of interest based upon the MCL components; (e) compensating the healthcare center according to the MCL components that contribute to the generation of the at least one $PM_1$. In one embodiment, the VL may be provided in a Model Deconstruction Transfer (MDT) platform.

In a further embodiment, there is provided a method of compensating a healthcare center based upon data provided by the healthcare center for use in the generation of a prediction model for a health outcome comprising the steps of: (a) obtaining at least one data set relevant to the health outcome of interest from more than one healthcare centers; (b) selecting variables from the at least one data set that are relevant to the health outcome of interest; (c) generating at least one first prediction model ($PM_0$) for the healthcare center based upon the differential weighting of the variables; (d) generating a Model Component Library (MCL) from the at least one $PM_0$, wherein the MCL comprises components that result from deconstruction of the $PM_0$; and (e) generating at least one second prediction model ($PM_1$) for the health outcome of interest based upon the MCL components; and (f) compensating the healthcare center according to the MCL components that contribute to the generation of the at least one $PM_1$. In one embodiment, the at least one data set may be provided in a Model Deconstruction Transfer (MDT) platform comprising a variable library (VL).

In another embodiment, factors determining the healthcare center's compensation are selected from the group consisting of size or existence of the healthcare center's data, amount or variety of variables selected by the healthcare center, amount and/or quality of data missing from the data provided by the healthcare center, and contribution of MCL components derived from the at least one $PM_0$.

In further embodiments, the healthcare center may be compensated according to a percentage of revenue share based upon contribution of MCL components derived from the at least one $PM_0$ that are instrumental to performance of the at least one $PM_1$. For example, the healthcare center may be compensated according to a fixed payment per measure of MCL components used in the at least one $PM_1$.

Additional aspects and embodiments of the invention will be provided, without limitation, in the detailed description of the invention that is set forth below.

DETAILED DESCRIPTION OF THE INVENTION

Figure 1:
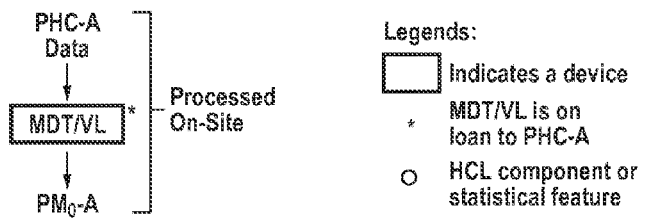
FIG. 1 is a schematic representation of an embodiment of the invention where a single PHC has access to a single on-site MDT/VL platform and a single prediction model ($PM_0$) is generated.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

The terms "healthcare center" and "healthcare facility," which are used interchangeably herein, are meant to refer to and include all types of healthcare-related institutions, including without limitation, institutions servicing inpatient care, outpatient care, acute care, subacute care, long term care, rehabilitative care, palliative care, urgent care, emergency care, trauma centers, tertiary care, community care, and rural care.

The term "participating healthcare center" or "PHC" is meant to include healthcare centers that are used to prepare a prediction model under the methods of the present invention.

As used herein, the term "client" refers to any third party that may interact with a healthcare center. Such clients include, without limitation, any of the following: an insurance company; a health management organization (HMO); a network of healthcare providers; Medicare and/or Medicaid; a federal, state or local government; a native tribunal; a military branch; a pharmaceutical, biotech, and/or medical device company; a third party payer (e.g., a self-insured large employer); one or a group of healthcare centers, such as hospitals, outpatient clinics, and community clinics; specialty practices, such as oncology, hemodialysis, fertility, and ophthalmology practices; transplant and organ donation agencies; professional organizations (e.g., American Medical Association); charitable foundations; and global health projects, including private, non-profit, or government funded projects.

As used herein, the term "source," "sources" and "multiple sources" is used to refer to one or more healthcare centers.

The term "healthcare provider" is meant to include physicians, nurses, nurse practitioners, nursing assistants, medical technicians, dentists, psychologists, homeopaths, chiropractors, or other healthcare professionals that are subject to the rules of conduct of a professional licensing body, and trainees of any of the above.

The term "patient" is meant to include any human person that is under the care of a healthcare provider. Within the context of the present invention, a patient may be, but is not necessarily undergoing a medical procedure and/or is ill.

The term "treatment" is meant to include any medical, behavioral, surgical, and/or procedural act or intervention that is provided by a healthcare professional through counseling or by way of a medical device. Treatments may be provided by the healthcare professional and/or device in a healthcare facility or alternatively, upon proper instruction by a healthcare professional or healthcare facility, treatments may be performed to be performed by the patient herself/himself.

The term "health outcome" is meant to refer to an adverse health condition of a patient, who is undergoing treatment for a specific disease state and/or condition. Examples of health outcomes within the context of the present invention include, without limitation, poor treatment response, worsening of a condition, rate of disease progression, probability of success following an interventional procedure, probability of failure following an interventional procedure, probability of complications following an interventional procedure, readmission to emergency services for a specific condition, readmission to a hospital for a specific condition, development of co-morbidities, and combinations of any of the foregoing.

The term "healthcare data" is meant to refer to medical data that is created in the process of inpatient or outpatient clinical services that are provided to the patient, such as for example, patient history, physical exams, lab tests and results, medical procedures and results, medications and patient response to the medications. As used herein, "healthcare data" is meant to include data that is generated for billing and other administrative tasks that are required for the patient to receive clinical services with his/her healthcare providers and navigate his/her healthcare needs, such as for example, pharmaceutical prescriptions, lab orders, billing records, and referrals.

The term "data set" is meant to refer to healthcare data provided by a healthcare center, which pertains to patients and/or medical cases. A data set will typically be extracted by a healthcare center either electronically (through for example, an electronic query) or manually, or through a combination of electronic and manual means. The healthcare data in a data set may or may not include personal identifiers (a data set void of personal information known in the art as a "de-identified data set"). Within the context of the present invention, a data set from a particular healthcare center (i.e., a "data source") will typically be relevant to the healthcare outcome for which a prediction model is built.

The term "test set" is meant to refer to a data set that is prepared from data provided by a PHC or a non-PHC (see, Examples 2-6) that is used to validate a prediction model. In other words, a prediction model is applied to a test dataset to see how well the prediction model performs. Within the context of the present invention, test sets are typically directed to datasets from years that are close to or current to the year of the prediction model.

The term "training set" is meant to refer to a data set that is prepared from data provided by a PHC or a non-PHC (see, Examples 2-6) that is used to generate or train one or more prediction models for a particular condition or disease state. Within the context of the present invention, training sets are typically directed to datasets from years that are further removed (in the past) to the year of the prediction model.

The term "electronic health records" or "EHR" is meant to include healthcare facility-hosted electronic medical records (EMR), internet-based EHR, data input by healthcare providers (including designated personnel), and patients and/or consumers.

The term "storage medium" and "electronic storage medium" includes without limitation, an external hard drive, a CD ROM, a USB memory device (also referred to as a "memory stick" and a "thumb drive"), an electronic mobile device (such as a smart phone, tablet computer, notebook computer, or laptop computer), a desktop computer, a server (including a closed network of servers inaccessible to the public), a VPN, a secure internet website, and software product that is downloadable from the internet with security features. Security features include without limitation, digital certificates, user access codes, auto-expiration dates, and anti-de-encryption mechanisms.

The term "server" is meant to refer to a stand-alone computer and/or a networked server that is dedicated to carry out a subject operation. Examples of stand-alone and networked servers that may be used with the present invention include without limitation, a desktop, a laptop, a mobile device, a co-location server, a local on-site server, and an off-site cloud server. Cloud servers include public cloud servers and private/dedicated cloud or hybrid cloud servers.

As used herein, the term "control model" refers to a prediction model, or practice guidelines, or eligibility criteria (e.g. criteria required to perform a medical service, provide coverage to a medical service, or to reimburse healthcare professionals or healthcare facilities), that is in standard use in the healthcare industry or that is being more specifically used for the generation of a prediction model by a specific PHC.

As used herein, the term "baseline" refers to an overall mean probability, disregarding any profiling or modeling. With reference to a control model, the baseline is the average probability if no predictive modeling is done. If no prior model exists, a control model may be generated by using one or more variables that are commonly used by healthcare providers in a particular situation.

The terms "Model Deconstruction and Transfer" and "MDT" are meant to refer to a platform that allows the PHC to provide access to a third party, to use a PHC's healthcare data to generate a prediction model that is devoid of any personal identifiers on-site, and transfer that prediction model to a third-party facility, without the transfer of personal identifiers or any raw data, for deconstruction. One example of an MDT platform that may be used with the present invention is an electronic storage medium that contains the MDT platform and allows a PHC to access the MDT platform.

The terms "Variable Library" and "VL" are meant to refer to the variables that are provided in the MDT platform of the present invention; the terms are meant to include all variables and subsets of variables that may populate the MDT platform. Examples of VLs that may be used within the context of the present invention, include without limitation, patient demographics, patient insurance policy status, patient billing data, patient family history, patient laboratory results, patient imaging results, patient pathology results (tissue biopsies), patient immunopathology results, patient cytology results, patient cytogenetic results, patient gene expression, patient metabolic panels, patient metabolic profiles, patient genomic data, patient response to procedures, patient medications, patient therapeutic regimens, patient acute care parameters, patient ambulatory monitoring; frequency of outpatient visits, frequency of emergency visits, frequency of hospital admissions, frequency of hospital re-admissions; quality of life assessments; clinical characteristics (clinical signs and symptoms), clinical diagnoses, clinic inpatient procedures, clinic outpatient procedures; monitoring for cancer recurrence, psychiatric assessments; and CPT (current procedural technology) diagnostic codes.

The terms "MCL," "Model Component Library," and "MCL components" are meant to refer to the deconstructed components derived from statistical features of prediction models ($PM_O$). Each MCL component represents a statistical feature that pertains to one or more variables provided in a data set, a VL, or a combination of both. The terms include all of the components that comprise the MCL as well as all subsets of components included therein. Within the context of the present invention, the MCL components may be derived from PHC-derived prediction models ($PM_O$) by way of an MDT platform (see, e.g., FIG. 2) or the MCL components may be derived directly from PHC-derived prediction models ($PM_O$) that has not been analyzed through an MDT platform (see, e.g., FIG. 4). Examples of MCLs that may be used within the context of the present invention include, without limitation, patient demographics, patient insurance policy status, patient billing data, patient family history, patient laboratory results, patient imaging results, patient pathology results (tissue biopsies), patient immunopathology results, patient cytology results, patient cytogenetic results, patient gene expression, patient metabolic panels, patient metabolic profiles, patient genomic data, patient response to procedures, patient medications, patient therapeutic regimens, patient acute care parameters, patient ambulatory monitoring; frequency of outpatient visits, frequency of emergency visits, frequency of hospital admissions, frequency of hospital re-admissions; quality of life assessments; clinical characteristics (clinical signs and symptoms), clinical diagnoses, clinic inpatient procedures, clinic outpatient procedures; monitoring for cancer recurrence, psychiatric assessments; and CPT (current procedural technology) diagnostic codes.

In order to achieve useful prediction models for a health outcome of interest, it is necessary to have a data set comprised of patients with diverse clinical characteristics, preferably from multiple sources. Diversity of healthcare data is essential for applying prognostics that are meaningful to individuals within the general population, which includes atypical as well as typical patients. In its broadest terms, diversity of healthcare relates to the full spectrum of health and/or disease outcome predictors. In more specific terms, diverse healthcare data includes without limitation, clinical characteristics such as age, ethnicity, gender, body mass index; genetic predictors such as the presence of certain mutations, deletions, single nucleotide polymorphisms, sequences; metabolic or physiological predictors such as levels of certain metabolites or secreted factors in the serum, or physiological measures such as heart rate, and electrocardiogram data.

The challenge of extracting the most powerful health outcome prediction tools out of multiple data sources has remained despite advances in statistical and mathematical modeling. Some of the obstacles relate to non-standardization of EHR database structure; variable data entry due to different clinical protocols and workflow among healthcare centers; slow adoption of IT and network interoperability standards; inefficiencies, liabilities and thereby costs of data-sharing associated with legal- and institution-imposed protection of healthcare data that is linked to personal identifiers.

The present invention provides methods for harnessing the massive amounts of healthcare data that exist among multiple sources and turning that data into prediction models that are rich in diversity and prognostic value and are capable of being applied to patient populations that may or may not have accumulated years of healthcare data. Further, the methods of the present invention facilitate the building of prediction models that are based on diverse datasets from multiple sources without the need to de-identify the healthcare data or to physically transfer any identifying or de-identified data from the healthcare center. In practice, a participating healthcare center (PHC) enters its dataset into a Model Deconstruction and Transfer (MDT) platform, which is installed in the virtual or physical property of the PHC. The MDT platform includes a variable library (VL), which allows the PHC to select variables that will be used to generate and validate the prediction model. Once the prediction model is established, the PHC may further utilize the MDT platform to extract statistical features and/or components from the prediction model and send those features and/or components to a third party who can in turn reassemble the statistical features and/or components, together with statistical features and/or components from other facilities (i.e., the multiple sources), into a Model Component Library (MCL). The multi-source-derived MCL may be applied to other data sets to train and/or validate prediction models that represent diverse patient profiles originating from multiple sources.

An advantage of the methods described herein is that the healthcare-related data sets never need to leave the physical or virtual site of the PHC. Importantly, any MCL-generated statistical features and/or components that are sent to the third party are void of any personal identifiers.

Examples 1-6 describe the generation of prediction models according to the present invention. Example 1 describes an exemplary method by which first prediction models ($PM_O$) relating to the success rate of intrauterine insemination (IUI) are generated for each of five clinics, i.e., PHC-A to PHC-E. Example 2 describes the generation of a second prediction model ($PM_1$) relating to the ER readmission rate for asthma patients in a generalized population derived from two tertiary centers (PHC-A and PHC-B) and three community hospitals (PHC-C to PHC-E). Example 2 also describes how each of the five PHCs is compensated for their contribution to the generation of the $PM_1$. Examples 3 and 4 provide examples of how the MCL of the present invention may expand the predictive scope of a healthcare center that does not have sufficient data to develop its own predictions for a health outcome of interest. In Example 3, a non-PHC regional healthcare network wants a prediction model for IUI treatment successes, but has very little date of their own. In Example 4, PHC-E wants a customized prediction model that expands the scope of its $PM_O$ beyond its core patient population. In both examples, Company A prepares an MCL from the five $PM_O$ of Example 1 and deconstructs the data in the MCL to generate a customized $PM_1$ that predicts IUI treatment successes in populations that exceed those specific to the non-PHC regional healthcare network (Example 3) and PHC-E of Example 4. Example 5 describes a method by which first prediction models ($PM_O$) for three diabetic conditions (retinopathy, renal disease, and high serum LDL cholesterol) are generated for three clinics (i.e., 9 $PM_0$ generated). Each $PM_0$ specific to each condition is deconstructed into its basic components to prepare an MCL specific to the particular condition (i.e., 3 MCLs prepare). Each MCL is then used to generate a second prediction model ($PM_1$) that is specific to each condition in a collective population of patients represented by each of the clinics. Example 6 describes a similar procedure as that described in Example 5, but the disease state is cancer and the disease progression is tumor recurrence and/or metastasis for a patient in remission over the next five years period. In this example, $PM_0$ data for three clinics is generated to produce 6 $PM_0$ values, which are deconstructed to prepare an MCL specific to each of the two conditions. The MCLs are then used to generate a $PM_1$ specific to each condition in a population of patients represented by each of the three clinics. In Examples 1-6, it is to be understood that the MDT platforms, the VLs, and the MCLs, including all variables and components in the MDTs, VLs, and MCLs, are owned by Company A. Lastly, it is to be understood that PHC may or may not charge Company A for data use for subjecting PHC's data to MDT platform may, but in any case, the PHCs will be responsible for preparing their own back-up copy of the data prior to the destruction of the data sets.

Figure 2:
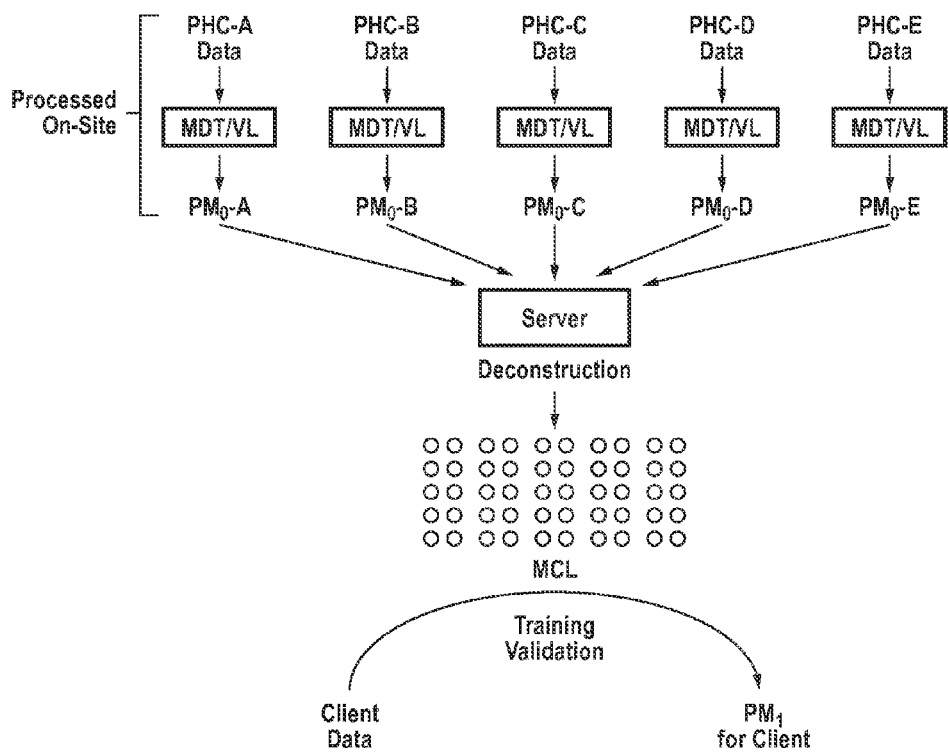
FIG. 2 is a schematic representation of an embodiment of the invention wherein five PHCs have individual on-site access to MDT/VL platforms which generate five first prediction models ($PM_0$) and an MCL, the latter of which is used to deconstruct the $PM_0$ to generate a single second prediction model ($PM_1$) directed to a health outcome of interest in a general population collectively representative of the five PHCs.
Figure 3:
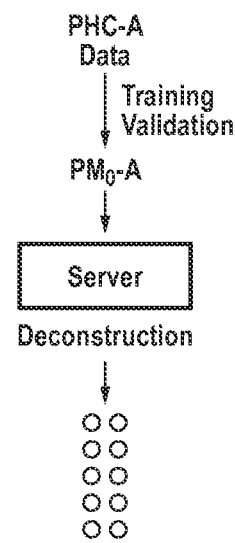
FIG. 3 is a schematic representation of an embodiment of the invention wherein data from a single PHC is used to generate a first prediction model ($PM_0$), an MCL, and a second prediction model ($PM_1$).
Figure 4:
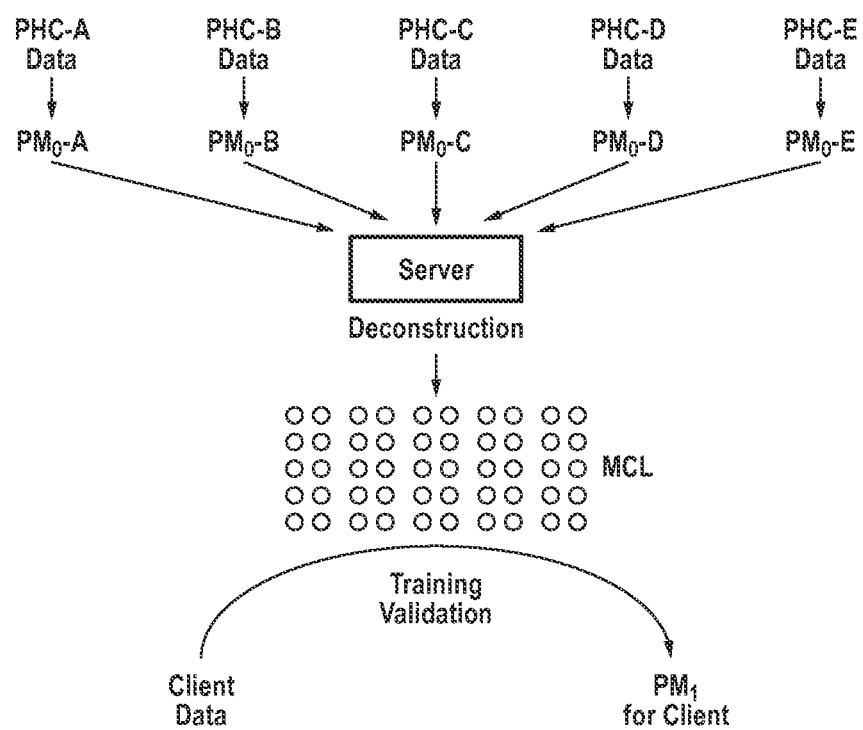
FIG. 4 is a schematic representation of an embodiment of the invention that does not involve application of an MDT/VL platform, where the data from five PHCs is used to generate five first prediction models ($PM_0$) and an MCL, the latter of which is used to deconstruct the $PM_0$ to arrive at a single second prediction model ($PM_1$) directed to a health outcome of interest in a general population collectively representative of the five PHCs.

In one aspect of the invention, each $PM_0$ may be deconstructed to form an MCL, which parses each of the variables that comprise the $PM_0$ into individual components. FIGS. 2-4 show a schematic of the deconstruction process of the present invention. The deconstruction process extracts each and all statistical features from each $PM_0$ to from an MCL. As shown in FIGS. 2-4, the deconstruction process is most effectively carried out by a server. The MCL of the present invention is used to generate a second prediction model $PM_1$, which is capable of providing an accurate prediction of the health outcome of interest for individuals in a broad population that is represented by the collective population of each of the PHCs involved in a particular project.

The $PM_0$ is deconstructed into statistical features of which the MCL is comprised. These statistical features, or MCL components, include without limitation, the individual predictive variables of the $PM_0$, or a part of the $PM_0$, and the value ranges or thresholds of the $PM_0$, or part of the $PM_0$, that has predictive value; the relative contribution of the predictive variables and associated value ranges; subsets of the predictive variables and associated value ranges or thresholds that have predictive value; use of subsets of the predictive variables and thresholds to optimally define patient populations that are enriched for a certain trait, prognosis or outcome; predictive power; discrimination; and reclassification. Where more than on $PM_1$ is generated from an MCL, the same statistical features (also referred to herein as "model performance parameters") may be used to generate, rank, and select between the more than one $PM_1$.

Predictive Power is measured by posterior probability conditioned upon a set of parameters; it may be expressed in terms of log likelihood, posterior probability of odds ratio (log scale or linear scale), and/or percentage of improvement in log likelihood. Discrimination refers to how well a model can differentiate patients with higher versus lower probabilities of outcomes, or those with significantly different prognoses. The ability to discriminate can be measured by receiver operator characteristics analysis, where the area-under-the-curve (AUC) indicates the degree of discrimination and AUC=0.5 indicates the model has no ability to discriminate. Reclassification is a measure of utility, and refers to the percentage of patients for whom the prediction model provides predicted probabilities that are significantly different from probabilities predicted by the control model (95% Confidence Interval).

It is to be understood by those of skill in the art that descriptions of a predictive model typically include estimated error ranges, which may be different for different percentile ranges of predicted probabilities (e.g., quartiles or quintiles); dynamic range, which refers to the range of probabilities that can be predicted. In addition to the foregoing, one of skill in the art will typically calculate the frequency of predicted probabilities obtained from a prediction model. Alternatively, the percentile rankings may be correlated with thresholds of predicted probabilities (e.g. the top 10 percentile of patients have ≥50% predicted probability of having a certain outcome.) Within the context of the present invention, the frequency of predicted probabilities will be directed to a particular patient population for which the prediction model is being validated, after it has been generated from MCL components (or statistical features).

In another embodiment of the invention, the entire dataset of a PHC may be used as a training set to develop one or more prediction models with each prediction model addressing a specific clinical outcome. In this case, it is to be understood that the prediction models made according to this embodiment will themselves not be validated, but a prediction model that is built with the help of MCL derived from this PHC's prediction model for a client will be subjected to validation using the client's test set.

In a further embodiment, a PHC may provide a test set, in addition to the training set. In this case, an MDT platform primarily serves as a mechanism to apply one or more pre-existing prediction models contained in the MDT platform (prediction models contained within an MDT platform are referenced by the terms $PM_0$, $PM_1$, $PM_2$, etc.) to the test set and measure how well the prediction models perform on the test set.

In another embodiment, the data set may be divided into non-overlapping training and test sets. The training set may be used by the MDT platform to build one or more prediction models. These prediction models may then be validated against the test set. The performance of each model is assessed by statistical tests during the validation process. The division of data into training and test sets may be accomplished by several methods, including, without limitation, chronologically, or randomly. A chronological test or training set generated from a data set spanning six years (e.g., 2005-2010) may comprise a test set comprised of data from the most recent years (i.e., the most recent 1-3 years available or 2008-2010) calculated from the date of the analysis, and a training set comprised of data from later years (i.e., the oldest three years available or 2005-2007) calculated from the date of the analysis. A randomly prepared test or training set may be generated with or without cross-validation, wherein many iterations of randomization are carried out and the medium performance of the randomization studies is measured. It is to be understood that the test and training sets described herein may also be prepared by more than one method; that is, for example, a test and training set may be generated through a combination of chronological and random methods.

In a further embodiment of the invention, a second data set is obtained from at least one of the more than one healthcare centers, wherein the second data set comprises healthcare data that pertains to a group of patients from a healthcare center that is not represented in the MCL and is non-redundant and unrelated to data used to generate the MCL.

In another embodiment of the invention, a second data set from at least one of the more than one healthcare centers, wherein the second data set comprises healthcare data pertaining to a group of patients from a healthcare center that is represented in the MCL, wherein the second data set is non-redundant to the first data set and the healthcare data that comprises the second data set is unrelated to the healthcare data used to generate the MCL.

In a further embodiment of the invention, there is provided a method for incentivizing PHCs to provide updated data, at regular time intervals, such as each year through effective compensation methods. With reference to Example 4, which describes a scenario where the client, i.e., the regional health network, is different from the PHC, the client pays Company A for producing a validated model that is generated from multiple sources via the use of the MDT platform and the MCL. The payment to Company A may be in the form of a project-based fee, which may be an upfront payment, or test-as-a-service model where the upfront payment is relatively small and the Company is paid on a per-test basis once the MCL is developed, validated, and available for use. The MCL can be made available for use via a stand-alone or EHR-supported DSS. Under this payment method, the PHCs are compensated not for licensing the use of their data, but for participating in the generation of the MDT platform and the MCL and for contributing to the predictive power of the final DSS tool. In one embodiment of the invention, Company A organizes participation of the PHCs, and compensates the PHCs for their participation and relative contribution to the predictive model. The compensation may be in the form of a flat fee, a fee that reflects a PHC's relative contribution to the performance of the prediction model, or a combination of the two. In another embodiment of the invention, the client organizes or requests the participation of designated PHCs, and Company A designs and executes the statistical and computation work. In the latter embodiment, the client compensates the PHCs directly, and also pays Company A for the resulting prediction model or the execution of the prediction model.

In another embodiment of the invention, the compensation may be applied to participation by the PHCs. Factors that impact the amount of compensation include without limitation, the size or existence of the dataset, the amount or variety of variables, and data quality (e.g. amount of missing data). In another embodiment of the invention, compensation is determined by contribution to the MCL components that are being selected for use in the final predictive model (i.e., the DSS tool). In this regard, there is no way for the PHC to know a priori, which model components will contribute most to prediction model validation that uses an independent data set. Presumably, consistency of operations, large data set size, multiple years of data all confer predictive power, but diversity in patients and their clinical attributes are also important factors. For example, a very small dataset that has an enrichment of a rare trait may contribute uniquely to a prediction model if the independent data set comprises individuals that also share this rare trait.

The compensation method described herein not only incentivize healthcare centers of varying sizes to participate, but also creates a disincentive for fraudulent attempts to improve a dataset, because it is not possible to know what kind of data will contribute the most predictive power nor is it possible to know which model components will be most useful in generating a prediction model for another population. The relative importance of variables also depends on the population for which a new model is being built. For example, different MCL model components may be required for two different clients (such as for example, two different regional healthcare networks whose patient populations have different characteristics). Compensation to the PHCs may be in the form of a percentage of revenue share (see, Example 2), a fixed payment per measure of MCL model components used, membership enrollment, or some other mutually agreeable terms.

In another embodiment of the invention, one or more third parties may license the right to use prediction models that have been built from multiple sources via the MDT/VL/MCL methods described.

In a further embodiment of the invention, an MCL is generated without the use of the MDT tool. Under this method, data from one or more PHC is obtained and variables specific to a health outcome of interest are selected from the data set. Using a computing method and the statistical criteria previously discussed, a $PM_0$ specific for each PHC is generated. The $PM_0$ may then be deconstructed to form an MCL, which may be used to generate a $PM_1$ specific to the health outcome of interest in a population that spans the more than one PHCs.

It is to be understood that the models provided herein are meant to be used to predict any disease state and are not specific and/or exclusive to the disease states described herein or in the examples and/or claims that follow. In this regard, the foregoing description and the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

EXPERIMENTAL

The following examples are set forth to provide those of ordinary skill in the art with a complete disclosure of how to make and use the aspects and embodiments of the invention as set forth herein.

Example 1

Generation of a Prediction Model ($PM_0$) for Counseling Patients Regarding the Success of IUI Treatments This example describes the development of a decision support (DS) tool to provide the predicted probability of having an intrauterine pregnancy outcome after intrauterine insemination (IUI) treatment for individuals and couples that have not been able to conceive naturally.

Company A wishes to respond to a need in the fertility market to develop a DS tool to provide the predicted probability of having an intrauterine pregnancy outcome after IUI treatment for individuals and couples that have not been able to conceive naturally. In order to develop this DS tool that will serve a diverse population (e.g. rural, urban, East Coast, Mid-west, South, West Coast, and various ethnicities) in this country, Company A establishes a product development arrangement with 5 fertility clinics that collectively serve a diverse population.

Company A provides a Model Deconstruction and Transfer (MDT) platform on an external storage medium along with instructions, to each of five PHCs: PHC-A, PHC-B, PHC-C, PHC-D, and PHC-E. Each MDT is designed to build prediction models for a specific clinical outcome or set of clinical outcomes. The PHCs are instructed to prepare a dataset in spreadsheet format, or exportable to one of several input formats, that contains data pertaining to variables listed in the MDT's VL. Each PHC may have data for a different subset of variables in the VL, with some variables being available in more clinics than others. In addition, if a clinic has data pertaining to variables that are not in the VL, it can create new variables to add to VL. The PHCs do not need to use an identical set of variables, and the data input for the variables does not need to be normalized or standardized; in other words, the structure of the dataset does not need to follow the same rules.

The dataset may include PHI and personal identifiers, if permitted by the policies of the PHC and any applicable HIPPA regulations. Alternatively, this dataset may be a de-identified or limited data set, which contains dates, but not other personal identifiers. It is to be understood that the dataset from any particular PHC is not shared with Company A, any of the other PHCs, or any ultimate users.

Each PHC runs the MDT platform on-site (see, e.g., FIG. 1); thus, the dataset entered into the MDT platform does not leave the PHC's physical location and is not exposed to Company A. Upon completion of the MDT execution, the dataset is automatically destroyed, and a message confirming destruction is shown and can be printed (to paper or to a portable data file (pdf)) by the MDT. Because the storage medium and MDT product are owned by Company A, but are considered to be on loan to each PHC for the specific execution, the destruction of the dataset confirms that Company A will have no access to the data set. Upon destruction of the dataset, the MDT, which now contains the prediction model, $PM_0$, but not the dataset, is returned to Company A for the deconstruction of the $PM_0$, to generate statistical features, or components, of the MCL. The PHC has the option to validate the data in the MDT through the use of a test set, which is either generated from the PHC's dataset or provided by the PHC as a separate dataset that is entered into the MDT. The test data set is destroyed along with the training data set.

The MDT and external hard drive now contain a prediction model ($PM_0$) (which may or may not be validated depending on whether or not the PHC ran a validation test or training set) relating to the success of IUI treatments specific to each PHC. These prediction models ($PM_0$) do not contain any raw data or identifiers; rather, they are encoded prediction models representing the statistical relationships among variables that have predictive value for the particular PHC from which they are derived.

After Company A receives the five MDT platform and external storage media from each of the five PHCs, the $PM_0$ from each MDT platform is downloaded to Company A's secure server. Company A will review the performance of each $PM_0$, according to statistical tests that are determined a priori. Acceptable criteria for the performance tests may be predetermined or determined at the time of review. Based upon the performance of the $PM_0$, Company A is able to advise each PHC on how to use the $PM_0$ to provide their patients with information regarding the success rate of IUI treatments in their clinic.

Example 2

Generation of a Prediction Model ($PM_1$) for Identifying Patients with High ER Readmission Rates and PHC Compensation Model A small chain of community hospitals with ER facilities asks Company A to use MCL model components derived from the ERs of two tertiary centers (PHC-A and PHC-B) and three community hospitals (PHC-C, PHC-D, and PHC-E) to develop a DS tool to predict the probability of a patient returning to the ER after being discharged from the ER for an asthma attack. The DS tool will allow the hospital chain the option to establish or test a protocol by which asthma patients at high risk of returning to the ER will be subject to a follow-up procedure within a certain period of time in an outpatient setting in order to minimize the need to return to the ER.

Company A generates five first prediction models ($PM_0$) for each of the five PHCs using an MDT platform as provided in Example 1 to predict the likelihood of an asthma patient of each PHC returning to the ER after a first admission. Company A then generates an MCL from each of the five $PM_0$ and uses the components in the MCL to generate a single second prediction model ($PM_1$) that predicts the likelihood of an asthma patient returning to the ER after a first admission in a patient population that spans that of the five PHCs. The $PM_1$ is trained and validated using the client's own data.

The $PM_1$ is generated with MCL components from the five PHCs with the following contributions to predictive power: PHC-A 25%, PHC-B 40%, PHC-C 30%, PHC-D 4%, and PHC-E 1%. The hospital chain pays Company A for providing the $PM_1$. In turn, Company A allocates 5% of revenue to be shared with the five PHCs in a ratio according to their contributions to the predictive power of the $PM_1$, e.g., 25:40:30:4:1. Thus, PHC-A receives 1.25% of revenue paid to Company A; PHC-B receives 2.0% of revenue paid to Company A; PHC-C receives 1.5% of revenue paid to Company A; PHC-D receives 0.2% of revenue paid to Company A; and PHC-E receives 0.05% total revenue paid to Company A.

Example 3

Generation of a Prediction Model ($PM_1$) for a Non-PHC

A client regional healthcare network, asks Company A to build a customized DS tool to provide predicted probabilities of the outcome of IUI treatment to its healthcare providers and patients. The regional healthcare network has only started to offer IUI treatment in the past two years so it does not have sufficient data to generate and validate its own prediction model.

Company A uses the five prediction models ($PM_0$) of Example 1 to prepare an MCL that is used to generate a single second prediction model ($PM_1$) that shows the success rate of IUI treatments in a population of patients represented by the five PHCs of Example 1. The regional healthcare network's own data is used as a test set to validate the use of $PM_1$ in the client's patient population. The performance of $PM_1$ is assessed during validation according to the statistical tests described herein.

Example 4

Generation of a Customized Prediction Model ($PM_1$) for a PHC

PHC-E makes a request to Company A for a customized prediction model ($PM_1$) that is more predictive than the $PM_0$ generated according to Example 1, which is built and validated based on PHC-E's own data. Because PHC-E has a very small data set compared to the other four PHCs (see, compensation model of Example 2), PHC-E is interested to leverage the collective predictive power that can be harnessed from using the MCL of Example 3.

To prepare the customized prediction model, PHC-E provides Company A with a de-identified data set that is non-redundant and independent from the data set that was generated with the MDT platform of Example 1 to build $PM_1$ for PHC-E. Company A performs the same procedures as described in Example 3 for the regional healthcare network to arrive at a $PM_1$ for PHC-E. The $PM_1$ is validated with a test and training set derived from PHC-E's own data.

Example 5

Generation of Prediction Model ($PM_1$) for Identifying Patients with Diabetes that have a High Risk of Disease Progression within a Specified Time Period A client hospital clinic wishes to develop a DS tool to identify diabetic patients that have a high probability of disease progression in specific areas such as retinopathy, renal disease, and high serum LDL cholesterol level within 6 months. Company A obtains data sets from three PHCs (PHC-1 to PHC-3) to generate nine individual first prediction models ($PM_0$): three $PM_0$ for PHC-1, each $PM_0$ specific for progression of the three disease states (i.e., retinopathy, renal disease, and high serum LDL cholesterol) in diabetic patients in a six-month period; three $PM_0$ for PHC-2, each $PM_0$ specific for each of the three disease states; and three $PM_0$ for PHC-3, each $PM_0$ specific for each of the three disease states. Variables included in the data sets that are used to prepare the $PM_0$ values, include without limitation, full blood and urinalysis panels over a specified period of time; data from eye exams and retina maps over a specified period of time; patient history relating to the frequency, occurrence and/or reoccurrence of kidney infections, gender, age, BMI, and patient nutritional and lifestyle habits. The nine $PM_0$ are used to prepare three MCLs with each MCL specific for each disease state. Each of the three MCL is used to generate each of three second prediction models ($PM_1$), which are able to predict the progression of retinopathy, renal disease, and high serum LDL cholesterol, respectively, in diabetic patients in a six-month period, across a patient population that is thought to be represented by the collective populations of PHC-1 to PHC-3. The DS tool comprising the three $PM_1$ values will allow the client to identify at-risk patients to enroll in a new management plan that provides more frequent visits, monitoring, and education, with the goal of decreasing the rate of disease progression.

Example 6

Generation of Prediction Model ($PM_1$) for Identifying Patients with Cancer that have a High Risk of Disease Progression within a Specified Time Period A client cancer clinic wishes to develop a DS tool to identify cancer patients in remission that have a high probability of disease progression in the form of tumor recurrence and/or metastasis. Company A obtains data sets from three PHCs (PHC-1 to PHC-3) to generate six individual first prediction models ($PM_0$): two $PM_0$ for each of PHC-1, PHC-2, and PHC-3, with each $PM_0$ specific for progression of the two disease states (i.e., tumor recurrence and tumor metastasis) in cancer patients in a five year period. Variables that are included in the data sets that are used to prepare the $PM_0$ values include, without limitation, known cancer biomarkers, gender, age, BMI, molecular diagnoses, pathological subtyping, health history, and patient response to previous treatments. The six $PM_0$ are used to prepare two MCLs, one for each disease state. The two MCLs are used to generate two second prediction models ($PM_1$), which are able to predict the progression of tumor recurrence and tumor metastasis, respectively, in cancer patients who are currently in remission for the next five years across a patient population that is thought to be represented by the collective populations of PHC-1 to PHC-3. The DS tool comprising the two $PM_1$ values will allow the client to identify at-risk patients to enroll in a new management plan that provides more frequent visits, monitoring, and education, with the goal of detecting tumor recurrence and/or metastasis earlier, so that treatments may be considered and initiated sooner to stop disease progression.

We claim:

1. A system for generating a prediction model for a health outcome of interest comprising:
   (a) a plurality of electronic storage media, each comprising a Model Deconstruction and Transfer platform (MDT), wherein each electronic storage media configured for receiving data from only one of a plurality of healthcare centers, wherein the MDT is comprised of a variable library (VL) comprised of variables relevant to a health outcome of interest, wherein upon completion of data entry by a healthcare center, the MDT generates a first prediction model ($PM_0$) for the health outcome of interest, wherein the $PM_0$ represents a statistical relationship among the variables that are predictive of the health outcome of interest, and further wherein upon generation of the $PM_0$, the MDT automatically destroys the data entered into the electronic storage media; and
   (b) a server configured to receive the MDT and deconstruct the $PM_0$ from the electronic storage media received from each of the plurality of healthcare centers, wherein the server is configured to perform the following functions,
      (i) combine the $PM_0$ from the plurality of healthcare centers;
      (ii) generate a Model Component Library, MCL from each $PM_0$, wherein the MCL comprises components that result from deconstruction of each $PM_0$,
      (iii) generate at least one second prediction model, $PM_1$, from the MCL based upon differential weighting of the MCL components relevant to the health outcome of interest, wherein the at least one $PM_1$ provides a prediction of the health outcome of interest for individuals in a broad population, wherein the broad population is represented by the data entered into the MDT by the plurality of healthcare centers;
   wherein the system expands predictive scope of a healthcare center that does not have sufficient data to develop its own predictions for a health outcome of interest.

2. The system of claim 1, wherein upon completion of the data entry and the generation of the $PM_0$, the MDT automatically destroys the entered data.

3. The system of claim 1, wherein the health outcome of interest is selected from the group consisting of poor treatment response, worsening of a condition, rate of disease progression, probability of success following an interventional procedure, probability of failure following an interventional procedure, probability of complications following an interventional procedure, readmission to emergency services for a specific condition, readmission to a hospital for a specific condition, development of co-morbidities, and combinations of any of the foregoing.

4. The system of claim 1, wherein the MCL components are selected from the group consisting of patient demographics, patient insurance policy status, patient billing data, patient family history, patient laboratory results, patient imaging results, patient pathology results (tissue biopsies), patient immunopathology results, patient cytology results, patient cytogenetic results, patient gene expression, patient metabolic panels, patient metabolic profiles, patient genomic data, patient response to procedures, patient medications, patient therapeutic regimens, patient acute care parameters, patient ambulatory monitoring; frequency of outpatient visits, frequency of emergency visits, frequency of hospital admissions, frequency of hospital re-admissions; quality of life assessments; clinical characteristics (clinical signs and symptoms), clinical diagnoses, clinic inpatient procedures, clinic outpatient procedures; monitoring for cancer recurrence, psychiatric assessments; and CPT (current procedural technology) diagnostic codes.

5. The system of claim 1, wherein the $PM_0$ and the at least one $PM_1$ are calculated using a statistical techniques selected from the group consisting of machine learning, logistic regression, linear regression, non-linear regression, and combinations of any of the foregoing.

6. The system of claim 5, wherein the machine learning techniques are selected from the group consisting of classification tree methods, LASSO (least absolute shrinkage and selection operator), Bayesian network modeling, and combinations of any of the foregoing.

7. The system of claim 6, wherein the classification tree method is a boosted tree method.

8. The system of claim 1, wherein the $PM_0$ is validated by a test data set originating from one or more of the healthcare centers.

9. The system of claim 8, wherein performance of the validated $PM_0$ is measured by comparison against performance of a control model.

10. The system of claim 1, wherein the at least one $PM_1$ is validated by a test data set originating from one or more of the healthcare centers.

11. The system of claim 10, wherein performance of the validated $PM_0$ is measured by comparison against performance of a control model.

12. The system of claim 9, wherein the comparison is carried out by applying statistical criteria selected from the group consisting of predictive power based on posterior log likelihoods, predictive power based upon posterior probability of an event, predictive power based upon estimated errors of prediction, dynamic range of predicted probabilities, reclassification, frequency of predicted probabilities, cross-validation error, number of model components required, ease of implementation, computing time, discrimination, calibration, and reclassification.

13. The system of claim 11, wherein the comparison is carried out by applying statistical criteria selected from the group consisting of predictive power based on posterior log likelihoods, predictive power based upon posterior probability of an event, predictive power based upon estimated errors of prediction, dynamic range of predicted probabilities, reclassification, frequency of predicted probabilities, cross-validation error, number of model components required, ease of implementation, computing time, discrimination, calibration, and reclassification.

14. The system of claim 1, wherein the at least one $PM_1$ is generated from the MCL by using individual MCL components as variables in the at least one $PM_1$ with differential weighting.

15. The system of claim 14, wherein a single MCL component may be used more than once in a single $PM_1$.

16. The system of claim 15, wherein each use of a single MCL component is subject to a different statistical function.

17. The system of claim 1, wherein one of the plurality of healthcare centers provides an additional data set comprising healthcare data for a group of patients that are not represented in the MCL, wherein the additional data set and is non-redundant and unrelated to the data used to generate the MCL.

18. The system of claim 1, wherein one of the plurality of healthcare centers provides an additional data set comprising healthcare data for a group of patients that are represented in the MCL, wherein the additional data set is non-redundant and unrelated to the data used to generate the MCL.

19. The system of claim 17, wherein the additional data set comprises a training set.

20. The system of claim 18, wherein the additional data set comprises a training set.

21. The system of claim 17, wherein the additional data set comprises a test set.

22. The system of claim 18, wherein the additional data set comprises a test set.

23. The system of claim 17, wherein the additional data set comprises a combination of a test set and a training set.

24. The system of claim 18, wherein the additional data set comprises a combination of a test set and a training set.

25. The system of claim 23, wherein the additional data set is divided into training and test sets chronologically according to the year of origin of the healthcare data.

26. The system of claim 24, wherein the additional data set is divided into training and test sets chronologically according to the year of origin of the healthcare data.

27. The system of claim 19, wherein the at least one $PM_1$ comprises MCL components that are selected based upon the performance of the at least one $PM_1$ to predict probabilities of the healthcare outcome in the training set.

28. The system of claim 20, wherein the at least one $PM_1$ comprises MCL components that are selected based upon the performance of the at least one $PM_1$ to predict probabilities of the healthcare outcome in the training set.

29. The system of claim 21, wherein the at least one $PM_1$ comprises MCL components that are selected based upon the performance of the at least one $PM_1$ to predict probabilities of the healthcare outcome in the test set.

30. The system of claim 22, wherein the at least one $PM_1$ comprises MCL components that are selected based upon the performance of the at least one $PM_1$ to predict probabilities of the healthcare outcome in the test set.

31. The system of claim 1, wherein at least two $PM_1$ are generated, ranked, and selected according to model performance parameters selected from the group consisting of posterior log likelihoods, predictive power based upon posterior probability of an event, predictive power based upon estimated errors of prediction, dynamic range of predicted probabilities, reclassification, frequency of predicted probabilities, cross-validation error, number of model components required, and discrimination.

32. A system for compensating a healthcare center according to claim 1, comprising compensating the healthcare center based upon contribution to the at least one $PM_1$ made by the healthcare center.

33. The system of claim 1, wherein the VL comprises variables selected from the group consisting of patient demographics, patient insurance policy status, patient billing data, patient family history, patient laboratory results, patient imaging results, patient pathology results, patient immunopathology results, patient cytology results, patient cytogenetic results, patient gene expression, patient metabolic panels, patient metabolic profiles, patient genomic data, patient response to procedures, patient medications, patient therapeutic regimens, patient acute care parameters, patient ambulatory monitoring; frequency of outpatient visits, frequency of emergency visits, frequency of hospital admissions, frequency of hospital re-admissions; quality of life assessments; clinical characteristics, clinical diagnoses, clinic inpatient procedures, clinic outpatient procedures; monitoring for cancer recurrence, psychiatric assessments; and current procedural technology (CPT) diagnostic codes.

34. The system of claim 32, wherein the healthcare center's compensation is based upon factors selected from the group consisting of size or existence of the healthcare center's data, amount or variety of variables selected by the healthcare center, amount and/or quality of data missing from the data provided by the healthcare center, and MCL components derived from the $PM_0$ of the healthcare center that contribute to the generation of the at least one $PM_1$.

35. The system of claim 32, wherein the healthcare center is compensated according to a percentage of revenue share based upon contribution of MCL components derived from the $PM_0$ that are instrumental to performance of the at least one $PM_1$.

36. The system of claim 32, wherein the healthcare center is compensated according to a fixed payment per measure of MCL components used in the at least one $PM_1$.

* * * * *